United States Patent [19]

Watson et al.

[11] 4,320,754
[45] Mar. 23, 1982

[54] CONTROLLABLE PARTIAL REBREATHING ANESTHESIA CIRCUIT AND RESPIRATORY ASSIST DEVICE

[76] Inventors: Robert L. Watson, 14312 Piccadilly Rd., Silver Spring, Md. 20906; Robert L. Rayburn, 495 N. Hills Dr., Salt Lake City, Utah 84117

[21] Appl. No.: 106,286

[22] Filed: Dec. 21, 1979

Related U.S. Application Data

[63] Continuation-in-part of Ser. No. 840,400, Oct. 7, 1977, Pat. No. 4,188,946.

[51] Int. Cl.³ ............................................. A61M 16/00
[52] U.S. Cl. ............................ 128/204.25; 128/205.13; 128/205.17; 128/911
[58] Field of Search .................... 128/204.18, 204.25, 128/205.12, 205.13, 205.17, 205.19, 205.24, 205.25, 207.14, 207.15, 207.16, 910, 911, 912, 205.29, 203.12, 203.14, 203.25, 203.28, 203.29, 206.21, 206.28, 207.11, 207.12, 221, 275.1, 276

[56] References Cited

U.S. PATENT DOCUMENTS

| | | | |
|---|---|---|---|
| 2,409,343 | 10/1946 | Curtis | 128/221 |
| 2,675,803 | 4/1954 | Kaslow | 128/207.11 |
| 2,737,695 | 3/1956 | Sokolik | 128/139 X |
| 2,831,487 | 4/1958 | Tafilaw | 128/205.25 |
| 3,467,094 | 9/1969 | Goodman | 128/205.17 X |
| 3,473,529 | 10/1969 | Wallace | 128/205.13 X |
| 3,537,447 | 11/1970 | Gauthier et al. | 128/139 |
| 3,721,239 | 3/1973 | Myers | 128/910 |
| 3,788,326 | 1/1974 | Jacobs | 128/207.15 |
| 3,814,103 | 6/1974 | Fettel et al. | 128/207.18 |
| 3,825,004 | 7/1974 | Durden | 128/275.1 |
| 3,856,051 | 12/1974 | Bain | 128/204.18 |
| 4,007,737 | 2/1977 | Paluch | 128/911 |
| 4,055,173 | 10/1977 | Knab | 128/139 |
| 4,077,404 | 3/1978 | Elam | 128/205.13 X |
| 4,109,651 | 8/1978 | Steigerwald | 128/205.17 |
| 4,244,363 | 1/1981 | Moore, Jr. et al. | 128/205.17 |
| 4,265,235 | 5/1981 | Fukanaga | 128/205.17 |

FOREIGN PATENT DOCUMENTS

| | | | |
|---|---|---|---|
| 706316 | 4/1941 | Fed. Rep. of Germany | 128/204.18 |
| 1296652 | 5/1962 | France | 128/207.16 |
| 810517 | 3/1959 | United Kingdom | 128/207.14 |
| 1270946 | 4/1972 | United Kingdom | 128/207.14 |
| 2020384 | 11/1979 | United Kingdom | 128/910 |
| 2025239 | 1/1980 | United Kingdom | 128/911 |

OTHER PUBLICATIONS

Ayre, "Endotracheal Anesthesia for Babies: With Special Reference to Harelip and Cleft Palate Operations", *Anesthesia and Analgesia*, Nov.–Dec. 1937, pp. 330–333.
Mansell, "Bain Circuit: The Hazzard of the Hidden Tube", Canadian Anesthetic Society Journal, vol. 23, No. 2, Mar. 1976, p. 227.

*Primary Examiner*—Henry J. Recla
*Attorney, Agent, or Firm*—Gunn, Lee & Jackson

[57] ABSTRACT

An apparatus for resuscitating, administering anesthesia to, or administering respiratory care to a patient is shown which allows greater rebreathing of mixed expired gases thus improving humidification and heat retention in the inspired gases. The inhalation breathing circuit may include two concentric, non-kinking, corrugated tubes, one visually apparent within the other, for handling both fresh gases and mixed expired gases of the patient or the inhalation breathing circuit may consist of a spiralled inflow tube contained within the wall of the larger exhalation corregated tube. An adjustable exhaust pressure valve maintains a predetermined pressure range for the gas being delivered to-and-fro between a breathing bag and the patient. Expired gases vent through an anesthesia bacterial filter or may be scavenged to prevent environmental pollution. Suctioning of the patient may be performed without interrupting the fresh gas flow or ventilation to the patient.

9 Claims, 12 Drawing Figures

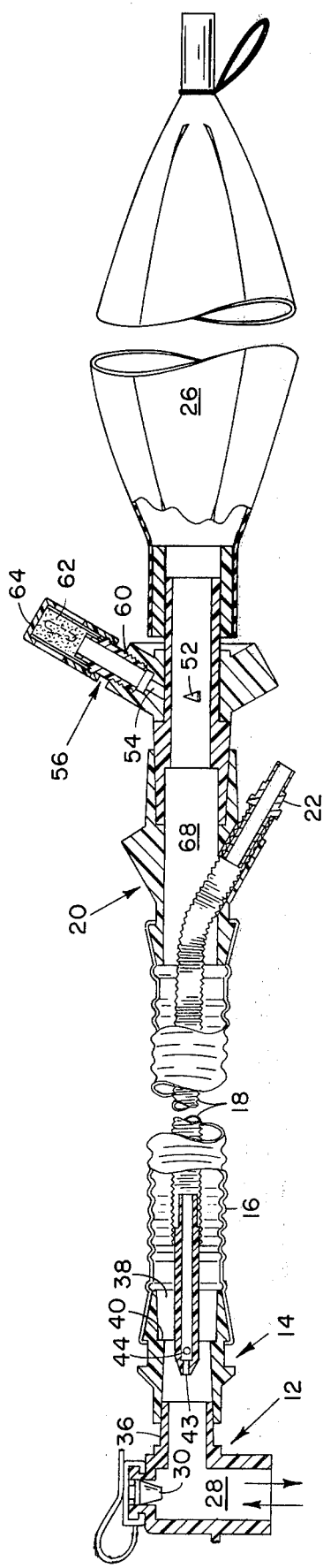
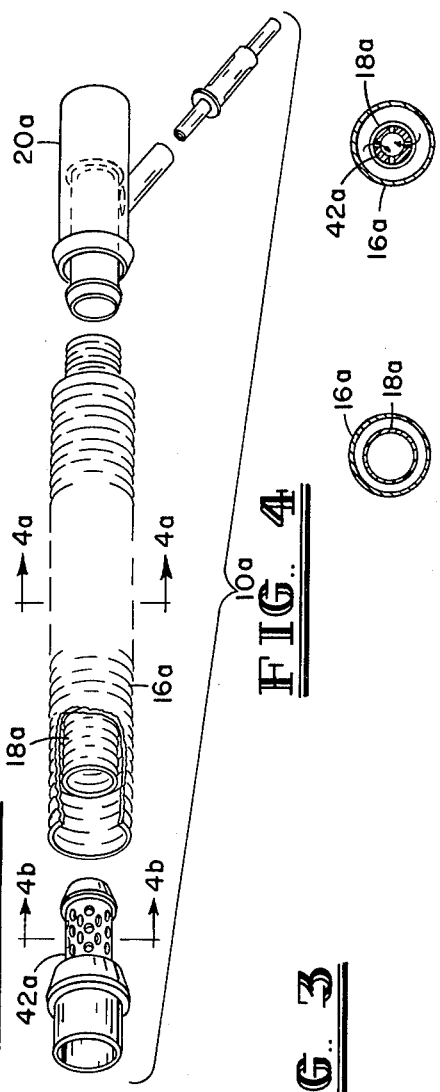
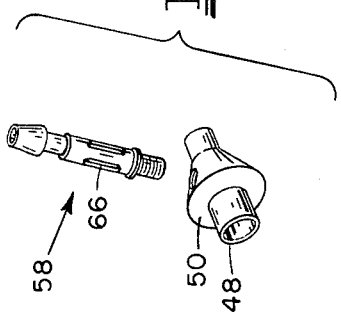
FIG. 2
FIG. 3
FIG. 4
FIG. 4a
FIG. 4b

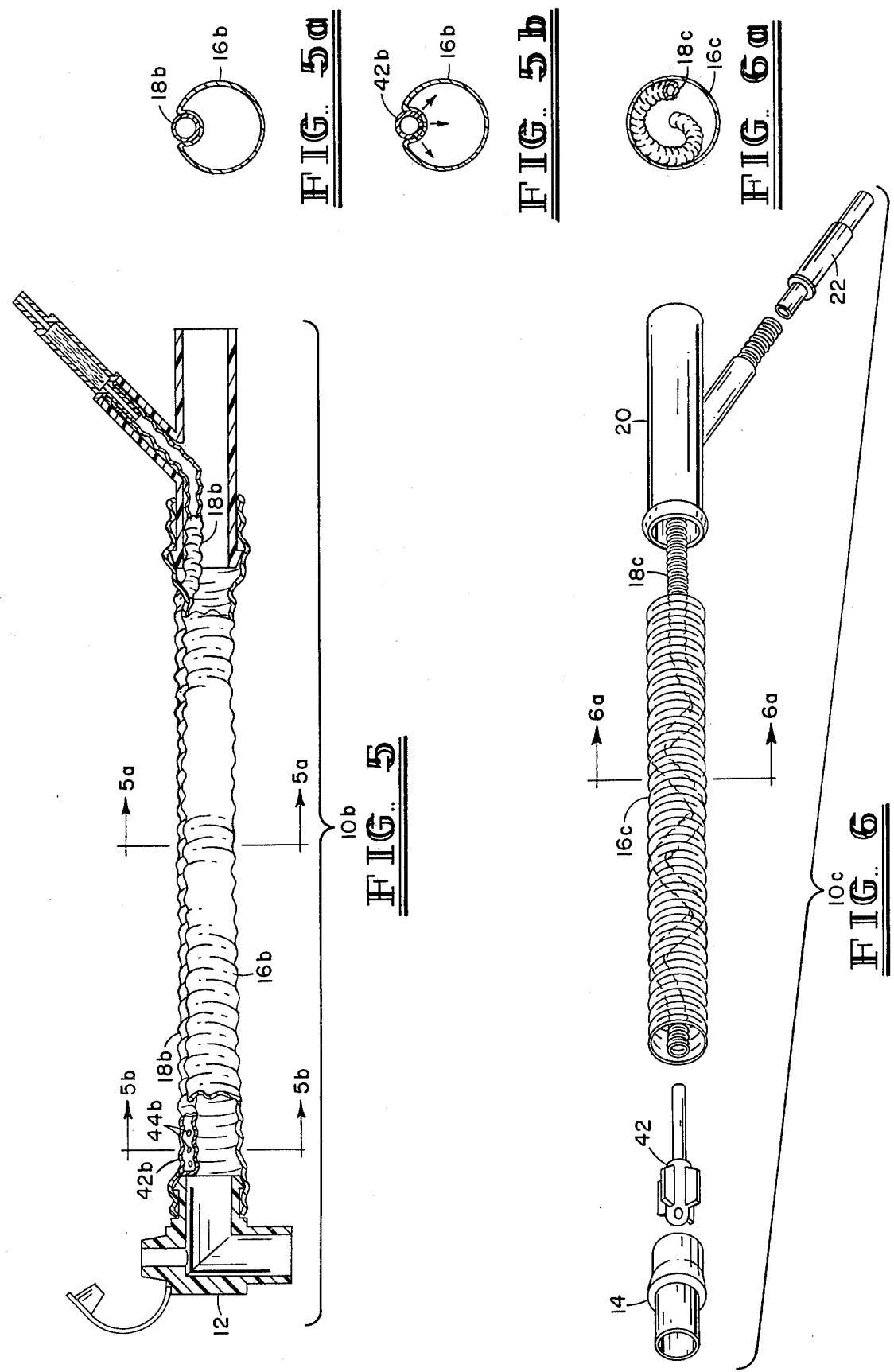

CONTROLLABLE PARTIAL REBREATHING ANESTHESIA CIRCUIT AND RESPIRATORY ASSIST DEVICE

BACKGROUND OF THE INVENTION

This application is a continuation-in-part of copending U.S. patent application Ser. No. 840,400 filed on Oct. 7, 1977 now Pat. No. 4,188,946 having the same inventors, which is hereby incorporated by reference.

SUMMARY OF THE INVENTION

The present invention is directed towards a controllable partial rebreathing anesthesia system and respiratory assist device. The rebreathing improves heating and humidification of the inspired gases which is not obtained by prior systems. The inhalation breathing circuit can be used in the field during emergencies or in the transportation of patients requiring supplemental oxygen, ventilation, end-expired pressure breathing, and tracheal suctioning. For greater safety and efficiency, the invented device may be connected to a control module as described in U.S. patent application Ser. No. 840,400.

A non-kinking corrugated tube is used as the fresh gas flow line and is connected to the fresh air supply externally where the integrity of the connection can be visually seen to avoid undetected disconnection. In addition, the fresh gas is delivered at the patient end by a substantially perpendicular discharge into the oscillatory flow of the patient's exhalation gases and inhalation gases. Such a delivery conserves the exhaled humidity by giving a cool circumferential screen of gas into which the patient exhales thereby causing a condensing of humidity at the patient end, prevents venturi gas flows which could create a vacuum in the exhalation tube that would be dangerous to certain patients, and efficiently mixes the gases.

The present invention prevents bacterial contamination of the hospital and ventilator with exhaled gases by attachment of an anesthesia filter, a disposable aerosal trap or hospital suction tube upon the exhaust valve.

The circuit may be used with an oxygen tank for transportation of the patient from one location to another. During transportation, positive end expiratory pressure can be maintained (via adaptability to a Carden valve).

An endotracheal tube elbow adapter is provided with a stoppered and sealed evacuation portal, the top of which may be removed to allow tight fitting suction tubes and/or flexible bronchoscopes to pass into the endotracheal tube and trachea for diagnosis and/or removal of secretions while maintaining volumetric pressure and oxygenation of the system. The lack of spring loaded type valves alleviates any difficulty concerning those types of springs malfunctioning.

BRIEF DESCRIPTION OF THE DRAWINGS

FIG. 1(a) is a cross-sectional view of FIG. 1 taken along lines 1(a)—1(a).

FIG. 2 is a cross-sectional view of FIG. 1 along lines 2—2.

FIG. 3 shows a modification wherein an exhaust outlet is attached to exhaust control valve.

FIG. 4 shows a modified version of the intake and expiration portions of the invention.

FIGS. 4(a) and 4(b) show cross-sectional views of FIG. 4 along lines 4(a)—4(a) and 4(b)—4(b), respectively.

FIG. 5 shows an additional modified view of the intake and expiration portions of the invention.

FIGS. 5(a) and 5(b) show cross-sectional views of FIG. 5 taken along lines 5(a)—5(a) and 5(b)—5(b), respectively, FIG. 6 shows an additional modification of the intake and expiration portions of the invention.

FIG. 6(a) is a cross-sectional view of FIG. 6 taken along lines 6(a)—6(a).

DESCRIPTION OF THE PREFERRED EMBODIMENT

Figure 1:
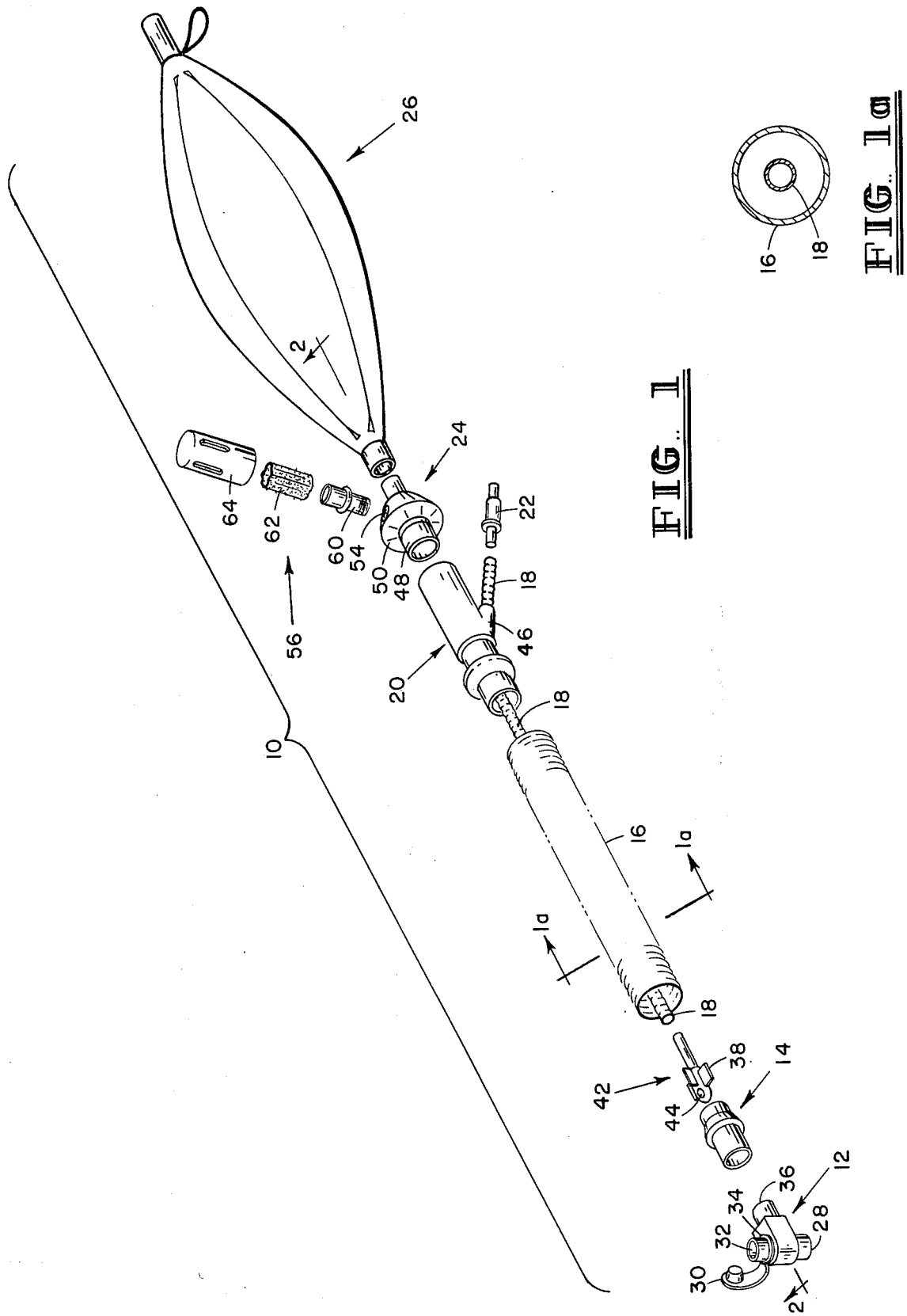
FIG. 1 is a perspective view of the invention showing concentric placement of the intake tube and expiration tube.

The main components of the rebreathing device 10 are the elbow adapter 12, mixing connector 14, exhalation tube 16, intake tube 18, circuit connector 20, fresh gas adapter 22, exhaust control 24, and reservoir bag 26 as shown in FIGS. 1 and 2.

Passage 28 of the elbow adapter 12 is adapted to fit upon or about a patient oral input, such as a mask or an endotracheal tube. Plug 30 fits securely within sealable opening 32 and fits within retaining ring 34 to ensure a continued seal by plug 30. Sealable opening 32 is located generally upon the elongated axis of passage 28 for allowing entry to the patient's lungs without interrupting the supply of fresh gas to the patient.

The posterior end of the elbow adapter 36 fits securely within mixing connector 14, which in turn fits securely within the patient end of exhalation tube 16. Radial flanges 38 fit upon inner shoulder 40 of the mixing connector 14 to hold intake delivery 42 in place. The posterior end of intake delivery 42 fits within intake tube 18 which delivers fresh gas through intake delivery 42 and out through end port 43 and side ports 44.

Intake tube 18 is located concentrically through exhalation tube 16, as shown in FIG. 1(a), with sufficient annular space between the tubes 16 and 18 to provide an air passage from the patient having a predetermined reservoir capacity of air. Circuit connector 20 fits within exhalation tube 16 and upon exhaust control 24 as shown. Intake tube 18 is positioned through intake tube holder 46 and extends out of circuit connector 20 to a junction with fresh gas adapter 22.

Exhaust control 24 consists of a pair of closely fitting cylinders, inner cylinder 48 and outer cylinder 50. Cylinder 48 has a wedge-shaped opening 52 about which hole 54 of the outer cylinder 50 may be rotated as a valve to give varying outlet diameters from within to without exhaust control 24. The outer portion of hole 54 is threaded to allow threadable attachment of either a bacterial filter 56, as shown in FIGS. 1 and 2, or an exhaust outlet 58, as shown in FIG. 3, and which may be connected to an aerosal trap or a hospital suction tube. Bacterial filter 56 comprises a radial stem 60 fitting within hole 54, filter 62, and filter housing 64. Openings 66 upon exhaust outlet 58 allow suction tubes to be used upon it without creating a vacuum within the exhalation tube 16.

Reservoir bag 26 fits upon the posterior end of exhaust control 24 and is in communication therethrough with exhalation passage 68.

In operation, predetermined volumes and pressures of oxygen or other selected gases are introduced through fresh gas adapter 22, intake tube 18, and intake delivery 42, andare radially discharged through end port 43 and side ports 44 to within exhalation passage 68. Intake delivery 42 is located within exhalation passage 68 to be within the tidal exhalation/inhalation distance from the patient and thus the oxygen is inhaled by the patient. As oxygen enters the exhalation/inhalation area of exhalation passage 68, like quantities of expired gases are forced from exhalation passage 68 through exhalation tube 68, wedge-shaped opening 52, hole 54, and bacterial filter 56. Reservoir bag 26 is responsive to exhalation passage 68 pressure changes due to patient respiration and patient respiration rate and volume can be observed and modified thereby.

Attachment of fresh gas adaptor 22 upon compressed corrugations of intake tube 18 upon the outside of the device 10 allows the operator to maintain a visual check of the attachment at all times. Intake tube 18 is colored (for instance, blue) so that the intake tube 18/intake delivery 42 connection can be easily visualized. The orientation of intake tube 18 away from the patient's oral area is helpful in reducing clutter and confusion in the oral area. Both tubes 16 and 18 are corrugated to reduce the probability of crimping, and exhalation tube 16 is transparent to allow visual checking of the intake tube 18/intake delivery 42 connection.

Prior art respiratory circuits normally direct incoming gas directly at the patient. In the invented device 10, the radial discharge of incoming fresh gas through radially positioned side ports 44, in addition to an end port 43, causes the fresh gas to flow to within the oscillatory flow of the exhalation gases and inhalation gases within the patient end of exhalation tube 16. This prevents a venturi gas flow within exhalation tube 16 which could lead to a pressure buildup at the patient end of exhalation tube 16. This is especially critical in treating small children who cannot tolerate pressures appreciably above atmospheric pressure without damage to their lungs. Because of the localized nature of such a venturi caused pressure buildup at the patient end of the exhalation tube 16, the pressure buildup is often undetected by prior art respirators. The substantially perpendicular injection of the incoming fresh gas also mixes the fresh gas with the exhalation and inhalation gases much more efficiently than prior art respiratory circuits.

The 90° angle within elbow adapter 12 allows a linear route of entry to the patient's lungs through sealable opening 20, and passage 28 of elbow adapter 12 without interruption of respiratory assistance. Suctioning, observation with a fiberoptic bronchoscope, or other treatments through or upon the patient's oral area may thus occur during ventilation if the tools used seal sealable opening 32.

Due to patient exhalation/inhalation, gas flow through exhaust passage 68 will be partially oscillatory with the patient rebreathing a portion of exhaled gases left within exhalation passage 68 and breathing an amount of fresh gases delivered to exhalation passage 68 by intake tube 18 with each breath. The radial discharge arrangement causes the warm humid exhalation gases to pass through a cool circumferential screen of fresh gas resulting in condensation and thus retention of the exhaled humidity. Humidification and heat retention problems attendant to fresh gas inhalation are thereby reduced and inhaled gas humidity content is determined by regulating the flow and composition of fresh gas, and by the minute ventilation of the patient.

Reservoir bag 26 provides the system elasticity necessary to accomodate patient inhalation/exhalation. A pressure relief governor and/or alarm valve may be attached to the device to insure the exhaust control is set to maintain proper exhaust passage 68 pressure parameters and an oxygen sensor may be attached to monitor oxygen content of the inspired gases.

It is additionally contemplated that a hand-held resuscitator to ventilate the patient with or without a separate oxygen supply may be created by attachment of a self-inflating bag in place of reservoir bag 26 and addition of a Laeral type valve to the device 10 at the patient end of exhalation tube 16. Further, a one-way check valve may be added to gas adapter 22 to prevent expired gases from being expired back through gas adapter 22 to contaminate the fresh gas source. After use the device may either be disassembled for sterilization and reused in whole or in part, or it may be thrown away. The fresh gas source is normally connected to gas adapter 22 by means of fresh gas supply line which usually comprises a tube, hose, or any similar conduit for communicating the fresh gas from the fresh gas source to the gas adapter 22.

FIGS. 4–6(a) show alternative versions of the intake and expiration portions of rebreathing device 10. FIGS. 4, 4(a), and 4(b) show modified device 10(a) having a modified intake delivery 42(a), modified intake tube 18(a), and a modified circuit connector 20(a). FIGS. 5, 5(a), and 5(b) show modified device 10(b) having modified intake 18(b) molded within the external wall of modified exhalation tube 16(b). A mixing connector may be used or not used (as shown in FIG. 5), and modified intake delivery 42(b) is formed by creating modified side ports 44(b) through modified exhaust tube 16(b) and modified intake tube 18(b). FIGS. 6 and 6(a) show modified device 10(c) having modified intake tube 18(c) spiraled integrally with the wall of modified exhalation tube 16(c). Other variations among device 10 and modified devices 10(a), 10(b), and 10(c) are apparent from the drawings.

Preserved in all modifications are radial entry of fresh gas into exhaust passage 68, visual means of checking to assure the input circuit is complete, and means for providing controlled rebreathing of portions of expired gas.

It is apparent from the above description that improvements in the art of resuscitating, administering anesthesia to, or administering respiratory care to a patient are achieved by the instant invention. While the invention has been described in connection with the preferred embodiment, it is not intended to limit the invention to the particular forms set forth, but, on the contrary, it is intended to cover such alternatives, modifications, and equivalents as may be included within the spirit and scope of the invention as defined by the appended claims.

I claim:

1. An inhalation breathing circuit for supplying fresh gases to a patient from source of fresh gases comprising:
    a fresh gas tube having a fresh gas passage therethrough, said fresh gas tube having a first end including means adapted to be connected to a source of fresh gases and an opposite second end;
    an exhalation tube having an exhalation passage therethrough, said exhalation tube having a first end and an opposite second end, said fresh gas tube extended through said exhalation passage with both said second end of said exhalation tube and said second end of said fresh gas tube terminating immediately adjacent said patient;

a short mixing connector for connecting said second end of said exhalation tube to said patient;

tip means connecting to said second end of said fresh gas tube adjacent said patient, said tip means being located inside said short mixing connector, said tip means having radial passages for discharging said fresh gases radially inside said short mixing connector;

circuit connector means with a main exhaust passage therethrough having a first end connected to said first end of said exhalation tube and an opposite second end, a fresh gas tube opening in said circuit connector means for receiving said fresh gas tube therethrough and into said main exhaust passage; and exhaust control means having a cylindrical body with a longitudinal passage therethrough having one end connected to the second end of said main exhaust passage of said circuit connector means and an opposite second end, said opposite second end of said cylindrical body having means adapted to be connected to a reservoir bag, said cylindrical body having a discharge opening through a side of said cylindrical body extending laterally to said longitudinal passage, a sleeve with a lateral opening being rotatably mounted on said cylindrical body, said lateral opening being rotatably alignable with said discharge opening and being adapted for connection to an anesthetic scavenging system;

said sleeve being rotatable on said cylindrical body to vary amount of overlap between said discharge opening of said cylindrical body and the lateral opening of said sleeve which controls amount of gases discharged during use.

2. The inhalation breathing circuit of claim 1 comprising bacterial filter means inside a filter housing connected to said lateral opening of said sleeve, said gases discharged flowing through said bacterial filter means.

3. The inhalation breathing circuit of claim 2 comprising a reservoir bag connected to the opposite second end of said longitudinal passage of said cylindrical body of said exhaust control means.

4. The inhalation breathing circuit of claim 3 comprising elbow adapter means with an elbow passage therethrough, said elbow adapter means having one end connected to said short mixing connector and an opposite end adapted to be connected to said patient, an opening in said elbow adapter means in alignment with said opposite end, removable plug means in said opening to allow direct access to said patient for suctioning.

5. The inhalation breathing circuit of claim 1, 2, 3 or 4 wherein said fresh gas tube and said exhalation tube are corrugated tubes, said means adapted to connect said fresh gas tube to a source of fresh gases being clearly visible.

6. An inhalation partial rebreathing circuit for supplying fresh gases to a patient from a source of fresh gases comprising:

a corrugated fresh gas tube with a fresh gas passage therethrough said fresh gas tube having a first end including means adapted to be connected to a source of fresh gases and an opposite second end;

a corrugated exhalation tube with an exhalation passage therethrough, said exhalation tube having a first end and an opposite second end, said corrugated fresh gas tube being concentric with said exhalation tube, said exhalation tube second end and said fresh gas tube second end both terminating at a point immediately adjacent said patient;

a mixing connector generally cylindrical in shape for a portion thereof with a mixing passage therethrough and having one end connected to said second end of said exhalation tube and an opposite end adapted to be connected to said patient;

tip means with a central passage therein connected to said second end of said fresh gas tube, said tip means extending into said mixing passage and having a radial means for positioning said tip means along a longitudinal axis of said mixing passage of said mixing connector, said tip means having a forward end with a reduced opening therein and radial passages connecting said tip means and said mixing connector for radial discharge of said fresh gases into said mixing passage to insure mixing of said fresh gases with expired gases from said patient immediately adjacent with patient; and circuit connector with a main exhaust passage therethrough having one end connected to the first end of said exhalation tube and an opposite second end, a fresh gas opening extending laterally through said circuit connector and communicating with said fresh gas tube concentrically positioned with respect to said exhalation tube, wherein partially mixed expired gases are removed from said patient through said second end of said main exhaust passage and replaced by said fresh gases.

7. The inhalation partial rebreathing circuit as given in claim 6 wherein said fresh gas tube is located inside said exhalation tube, said tip means having a generally conical shaped forward end to reduce resistance to said expired gases of said patient, said reduced opening being at an apex of said concical shaped forward end also for discharging said fresh gases.

8. The inhalation partial rebreathing circuit as given in claim 6 wherein said radial means comprises radial fins which abut against an internal shoulder of said mixing connector, said mixing connector having an external shoulder receiving said exhalation tube thereover.

9. The inhalation partial rebreathing circuit as given in claim 6 wherein said inhalation tube is located inside said fresh gas tube, said mixing connector and said tip means forming an integral unit with said radial means being an inwardly directed flange for reducing diameter of said integral unit for connection to said exhalation tube.

* * * * *